US006738529B1

United States Patent
Crevier et al.

(10) Patent No.: US 6,738,529 B1
(45) Date of Patent: May 18, 2004

(54) ANALYSIS OF CHEMICAL DATA FROM IMAGES

(75) Inventors: Thomas Crevier, San Jose, CA (US); William B. Archibald, Hillsborough, CA (US); Marc Hornbostel, Palo Alto, CA (US); Dieter Schaefer, San Jose, CA (US); Thomas Boussie, Menlo Park, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/415,772

(22) Filed: Oct. 8, 1999

Related U.S. Application Data

(63) Continuation-in-part of application No. 09/227,558, filed on Jan. 8, 1999, which is a continuation-in-part of application No. 08/898,715, filed on Jul. 22, 1997, now Pat. No. 6,030,917.
(60) Provisional application No. 60/050,949, filed on Jun. 13, 1997, provisional application No. 60/028,106, filed on Oct. 9, 1996, provisional application No. 60/029,255, filed on Oct. 25, 1996, provisional application No. 60/035,366, filed on Jan. 10, 1997, provisional application No. 60/048,987, filed on Jun. 9, 1997, provisional application No. 60/028,105, filed on Oct. 9, 1996, and provisional application No. 60/035,202, filed on Jan. 10, 1997.

(30) Foreign Application Priority Data

Apr. 1, 1999 (WO) .............................. PCT/US99/07358

(51) Int. Cl.⁷ ................................................ G06K 9/36

(52) U.S. Cl. ....................... 382/282; 382/110; 382/128; 382/190; 382/218; 703/11; 703/12; 436/46; 436/47; 436/50

(58) Field of Search ............................... 382/278, 282, 382/283, 286, 291, 110, 113, 128, 129, 130, 133, 134, 140, 149, 165, 170, 209, 216, 219, 224, 295; 348/176, 177, 187, 189; 703/9, 11, 12; 436/46, 47, 50, 52, 53, 54

(56) References Cited

U.S. PATENT DOCUMENTS 3,030,917 A * 4/1962 Brown et al. ............... 118/413

(List continued on next page.)

FOREIGN PATENT DOCUMENTS

EP         0 535 881 A1    4/1993

(List continued on next page.)

OTHER PUBLICATIONS

M.T. Reetz et al., *Time–Resolved HR–Thermographic Detection and Screening of Enantioselectivity in Catalytic Reactions*, Angew. Chem. Int. Ed. 1998, vol. 37, pp. 2467–2650.

(List continued on next page.)

*Primary Examiner*—Bhavesh M. Mehta
*Assistant Examiner*—Yosef Kassa
(74) *Attorney, Agent, or Firm*—Fish & Richardson P.C.

(57) ABSTRACT

Computer programs and computer-implemented methods are disclosed for extracting and analyzing combinatorial chemical data from images. The invention receives a stream of data, identifies a plurality of regions of interest and determines a series of values for one or more regions of interest. The library includes a plurality of members. The data stream includes a series of images of the library. Each region of interest corresponds to a location in each of the images and to a location in the library. The series of values for each region includes a value for each of the images. Particular embodiments have the following features. The invention calculates a figure of merit for a library member from each series of values. The stream of data comprises a series of images generated at a frequency of greater than about 1, 6, 12 or 30 frames per second. The series of images is captured from a beginning of a combinatorial experiment to an end of a commercial experiment. The regions of interest are identified after the series of images has been captured. The images are infrared images. The figure of merit is an emittance change, a phase transition point or a thermoelectric figure of merit for a library member. Regions of interest are identified by a user and have a user-defined shape. The series of values for each region is determined based on a user-defined computation. A graphical representation of the figures of merit is displayed.

42 Claims, 16 Drawing Sheets

(1 of 16 Drawing Sheet(s) Filed in Color)

U.S. PATENT DOCUMENTS

| | | | | |
|---|---|---|---|---|
| 4,998,284 A | * | 3/1991 | Bacus et al. | 382/233 |
| 5,127,063 A | | 6/1992 | Nishiya et al. | 382/8 |
| 5,143,854 A | | 9/1992 | Pirrung et al. | 436/518 |
| 5,549,996 A | | 8/1996 | Bollen | 430/21 |
| 5,571,639 A | | 11/1996 | Hubbell et al. | 430/5 |
| 5,631,734 A | | 5/1997 | Stern et al. | 356/317 |
| 5,776,359 A | | 7/1998 | Schultz et al. | 252/62.5 |
| 5,792,610 A | * | 8/1998 | Witney et al. | 435/6 |
| 5,856,101 A | | 1/1999 | Hubbell et al. | 435/6 |
| 5,974,164 A | | 10/1999 | Chee | 382/129 |
| 5,991,028 A | * | 11/1999 | Cabib et al. | 356/346 |
| RE36,529 E | * | 1/2000 | Lewis et al. | 356/346 |
| 6,025,601 A | | 2/2000 | Trulson et al. | 250/461 |
| 6,030,917 A | | 2/2000 | Weinberg et al. | 502/104 |
| 6,044,212 A | * | 3/2000 | Flavin et al. | 703/6 |
| 6,101,265 A | * | 8/2000 | Bacus et al. | 382/133 |
| 6,184,389 B1 | * | 2/2001 | Hebert | 549/6 |
| 6,316,626 B1 | * | 11/2001 | Swayze et al. | 546/207 |

FOREIGN PATENT DOCUMENTS

| | | |
|---|---|---|
| WO | WO 96/11878 | 4/1996 |
| WO | WO 97/32208 | 9/1997 |
| WO | WO 99/34206 | 7/1999 |

OTHER PUBLICATIONS

H. Dersch & N. Amer, *Optical approach to thermopower and conductivity measurements in thin–film semiconductors*, Appl. Phys. Lett. vol. 45 (Aug. 1, 1984), pp. 272–274.

Xiao–Dong Sun et al., *Solution–Phase Synthesis of Luminescent Materials Libraries*, 1997, Adv. Mater., vol. 9, No. 13., pp. 1046–1049.

Earl Danielson et al., *A combinatorial approach to the discovery and optimation of luminescent materials*, Oct. 1997, Nature, vol. 389, pp. 844–848.

Eric W. McFarland and W. Henry Weinberg, *Approaches for Rapid Materials Discovery Using Combinatorial Methods*, 1998, Mat. Tech. 13.3, pp. 107–120.

Network Science, *Introducing MDL Screen*, downloaded on Nov. 15, 2002, http://www.netsci.org/Science/Screening/feature03.html.

J.J. Hanak, *The "Multiple–Sample Concept" in Materials Research: Synthesis, Compositional Analysis and Testing of Entire Multicomponent Systems*, 1970, Journal of Materials Sciences, pp. 964–971.

Gabriel Briceño et al., *A Class of Cobolt Oxide Magnetoresistance Materials Discovered with Combinatorial Synthesis*, Oct. 13, 1995, Science, vol. 270, pp. 273–275.

Xiao–Dong Sun et al., *Identification and optimazation of advanced phosphors using combinatorial libraries*, 1997, American Institute of Physics, vol. 70, No. 25, pp. 3353–3355.

Bernd Jandeleit et al., *Combinatorial methods in catalysis*, Dec. 1998, Baltzer Science Publishers, vol. 2, No. 2, pp. 101–123.

Linda C. Hsieh–Wilson et al., *Lessons from the Immune System: From Catalysis to Materials Science*, 1996, Acc. Chem. Res., vol. 29, pp. 164–170.

Robert F. Service, *High–Speed Materials Design*, Jul. 1997, Science, vol. 277, pp. 474–475.

Xiao–Dong Sun et al., *A Combinatorial Approach to Materials Discovery* Jun. 23, 1995, Science, vol. 268, pp. 1738–1740.

PCT International Search Report, PCT/US99/07358, Aug. 16, 1999.

Dersch et al., "Optical approach to thermopower and conductivity measurements in thin–film semiconductors", Applied Physics Letters, vol. 45, No. 3, Aug. 1, 1984, 272–274.

Georgiades et al., "IR emission Analysis of Temperature Profiles in Pt/SiO$_2$ Catalysts during Exothermic Reactions", Chem. Int. Ed. Engl. 26, No. 10, 1987, 1042–1043.

Hardisty et al., "Thermal Imaging in Electronics and Rotating Machinery", 32 nd Annual British conf. on Non–Destructive Testing, Sep. 14–16, 1993, pp. 73–78.

Holzwarth et al., "Detection of Catalytic Activity in Combinatorial Libraries of Heteroeneous Catalysts by IR Thermography", Angew. Chem. Int. Ed. 1998, 37 No. 19, pp. 2644–2647.

Lewis et al., "Fourier Transform Spectroscopic Imaging Using an Infrared Focal–Plane Array Detector", Anal. chem., 1995, 67, pp. 3377–3381.

Moates et al., "Infrared Thermographic Screening of Combinatorial Libraries of Heterogeneous Catalysts", American Chem. Soc., 1996, pp. 4801–4803.

Moates et al., "Infrared Thermographic Screening of Combinatorial Libraries of Heterogeneous Catalysts", Screening Catalyst Activity, 8/97, pp. 683–686.

Pawlicki et al., "Spatial Effects on Supported Catalysts", Chem. Eng. Progress, 2/87, pp. 40–45.

Reddington et al., "Combinatorial Electrochemistry: A Highly Parallel, Optical Screening Method for Discovery of Better Electrocatalysts", Science vol. 280, Jun. 12, 1998, pp. 1735–1737.

Taylor et al., "Thermographic Selection of Effective Catalysts from an Encoded Polymer–Bound Library", Science, vol. 280, Apr. 10, 1998, pp. 267–270.

* cited by examiner

ANALYSIS OF CHEMICAL DATA FROM IMAGES

CROSS REFERENCE TO RELATED APPLICATIONS

This is a continuation of and claims priority to International Application PCT/US99/07358, with an international filing date of Apr. 1, 1999, now abandoned, which is a continuation-in-part of commonly assigned, co-pending U.S. patent application Ser. No. 09/227,558, filed Jan. 8, 1999, which is a continuation-in-part of U.S. application Ser. No. 08/898,715, filed Jul. 22, 1997, and U.S. Provisional Application Nos. 60/050,949, filed Jun. 13, 1997; 60/028,106, filed Oct. 9, 1996; 60/029,255, filed Oct. 25, 1996; 60/035,366, filed Jan. 10, 1997; 60/048,987, filed Jun. 9, 1997; 60/028,105, filed Oct. 9, 1996; and 60/035,202, filed Jan. 10, 1997. Each of the foregoing applications is incorporated herein by reference in its entirety and is the basis of a claim for priority under 35 U.S.C.§119 or 120.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

The present invention relates to methods and computer programs for rapidly screening and characterizing materials by the analysis of data acquired from images.

In combinatorial chemistry, a large number of candidate materials are created from a relatively small set of precursors and subsequently evaluated for suitability for a particular application. As currently practiced, combinatorial chemistry permits scientists to systematically explore the influence of structural variations in candidates by dramatically accelerating the rates at which they are created and evaluated. Compared to traditional discovery methods, combinatorial methods sharply reduce the costs associated with preparing and screening each candidate.

Combinatorial chemistry has revolutionized the process of drug discovery. One can view drug discovery as a two-step process: acquiring candidate compounds through laboratory synthesis or through natural products collection, followed by evaluation or screening for efficacy. Pharmaceutical researchers have long used high-throughput screening (HTS) protocols to rapidly evaluate the therapeutic value of natural products and libraries of compounds synthesized and cataloged over many years. However, compared to HTS protocols, chemical synthesis has historically been a slow, arduous process. With the advent of combinatorial methods, scientists can now create large libraries of organic molecules at a pace on par with HTS protocols.

Recently, combinatorial approaches have been used for discovery programs unrelated to drugs. For example, some researchers have recognized that combinatorial strategies also offer promise for the discovery of inorganic compounds such as high-temperature superconductors, magneto resistive materials, luminescent materials, and catalytic materials. See, for example, U.S. Pat. No. 5,776,359 and co-pending U.S. patent application No. 08/898,715 "Combinatorial Synthesis and Analysis of Organometallic Compounds and Catalysts" (published as WO 98/03251), which are both incorporated herein by reference.

SUMMARY OF THE INVENTION

The invention provides computer programs and computer-implemented methods for extracting and analyzing combinatorial chemical data from images.

In general, in one aspect, the invention features a computer program for evaluating a combinatorial library including a plurality of members. The program includes instructions to receive a stream of data including a series of images of the combinatorial library; to identify a plurality of regions of interest, each region corresponding to a location in each of the series of images and to a location in the combinatorial library; to determine a series of values for one or more regions of interest, the series of values for each of the one or more regions including a value for each of the images; and to calculate from each series of values for the one or more regions a figure of merit for the library member at the corresponding library location.

Implementations of the invention can include one or more of the following advantageous features. Each region of interest corresponds to a plurality of pixels in each image and the series of values for a region of interest comprises an average value for each of the corresponding plurality of pixels in each of the images. The stream of data comprises a series of images generated at a frequency of greater than about 1 frame per second. The stream of data comprises a series of images generated at a frequency of greater than about 6 frames per second. The stream of data comprises a series of images generated at a frequency of greater than about 12 frames per second. The stream of data comprises a series of images generated at a frequency of greater than about 20 frames per second. The program further includes instructions to display a graphical representation of the figures of merit. The graphical representation includes a histogram. The series of images is captured from a beginning of a combinatorial experiment to an end of the combinatorial experiment and the plurality of regions of interest may be identified after the series of images have been captured or after one or more images in the series of images has been captured. The series of images includes a series of infrared images. The figure of merit comprises an emittance change for a library member. The figure of merit comprises a phase transition point for a library member. The figure of merit comprises a thermoelectric figure of merit for a library member. The instructions to identify a plurality of regions of interest comprise instructions to receive a first user input identifying one or more regions of interest, each region having a user-defined shape. The program further includes instructions to receive a second user input defining a computation for determining a series of values for each of the one or more regions of interest. The instructions to determine a series of values for each of the one or more regions of interest include instructions to compute each value in each series in accordance with the second user input. The computation is an average for a group of pixels corresponding to a region of interest.

In general, in another aspect, the invention features a computer program on a computer-readable medium for evaluating a combinatorial library including a plurality of members. The program includes instructions to receive a stream of data including a series of images of the combinatorial library; to receive a first user input identifying one or more regions of interest, each region having a user-defined shape and each region corresponding to a location in each of the series of images and to a location in the combinatorial library; to receive a second user input defining a computation for determining a series of values for each of the one or more regions of interest, each series of values including a value for each of the images; and to determine a series of values for each of the one or more regions of interest, each value in each series being computed in accordance with the second user input.

Implementations of the invention can include one or more of the following advantageous features. The program further includes instructions to calculate from each series of values for the one or more regions a figure of merit for the library member at the corresponding library location.

In general, in another aspect, the invention features a computer program for evaluating a combinatorial chemical experiment. The program includes instructions to receive a series of images of a combinatorial library, the library including a plurality of members, the series of images captured from a beginning of the experiment to an end of the experiment; to identify, after the series of images has been captured, a plurality of regions of interest, each region corresponding to a location in each of the series of images and to a location in the combinatorial library; and to determine a series of values for one or more regions of interest, the series of values for each of the one or more regions including a value for each of the images.

In general, in another aspect, the invention features a method for evaluating a combinatorial library including a plurality of members. The method includes receiving a stream of data including a series of images of the combinatorial library; identifying a plurality of regions of interest, each region corresponding to a location in each of the series of images and to a location in the combinatorial library; determining a series of values for one or more regions of interest, the series of values for each of the one or more regions including a value for each of the images; and calculating from each series of values for the one or more regions a figure of merit for the library member at the corresponding library location.

In general, in another aspect, the invention features a computer-implemented method for evaluating a combinatorial chemical experiment. The method includes capturing a series of images of a combinatorial library, the library including a plurality of members, the series of images being captured from a beginning of the experiment to an end of the experiment and storing the series of images in memory; after the series of images has been captured, identifying a plurality of regions of interest, each region corresponding to a location in each of the series of images and to a location in the combinatorial library; and determining a series of values for one or more regions of interest, the series of values for each of the one or more regions including a value for each of the images.

In general, in one aspect, the invention features a system for evaluating a combinatorial library including a plurality of members. The system includes means for receiving a stream of data comprising a series of images of the combinatorial library; means for identifying a plurality of regions of interest, each region corresponding to a location in each of the series of images and to a location in the combinatorial library; means for determining a series of values for one or more regions of interest, the series of values for each of the one or more regions comprising a value for each of the images; and means for calculating from each series of values for the one or more regions a figure of merit for the library member at the corresponding library location.

In general, in other aspect, the invention features a system for evaluating a combinatorial library, the library including a plurality of members. The system includes means for receiving a stream of data comprising a series of images of the combinatorial library; means for receiving a first user input identifying one or more regions of interest, each region having a user-defined shape and each region corresponding to a location in each of the series of images and to a location in the combinatorial library; means for receiving a second user input defining a computation for determining a series of values for each of the one or more regions of interest, each series of values comprising a value for each of the images; and means for determining a series of values for each of the one or more regions of interest, each value in each series being computed in accordance with the second user input.

In general, in other aspect, the invention features a system for evaluating a combinatorial chemical experiment. The system includes means for receiving a series of images of a combinatorial library, the library including a plurality of members, the series of images captured from a beginning of the experiment to an end of the experiment; means for identifying a plurality of regions of interest after the series of images has been captured, each region corresponding to a location in each of the series of images and to a location in the combinatorial library; and means for determining a series of values for one or more regions of interest, the series of values for each of the one or more regions comprising a value for each of the images.

Advantages that can be seen in implementations of the invention include one or more of the following. The use of a video image sequence allows the automated extraction of data from one or more regions in every frame of the image set. This results in a time-resolved profile of the reaction of transformation being observed, rather than merely snapshots based on a limited number of selected images or image frames. Regions of interest in each image can be defined after the image sequence is captured. Calculations and corrections can be applied automatically to every region in every frame of the image set. One or more figures of merit can be extracted from some or all of the data set for each region and can be graphically displayed.

The details of one or more embodiments of the invention are set forth in the accompanying drawings and the description below. Other features and advantages of the invention will become apparent from the description, the drawings, and the claims.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

Like reference numbers and designations in the various drawings indicate like elements.

DETAILED DESCRIPTION

In the present invention, a camera observes an experiment. The resulting image data is analyzed by a data processing system implementing methods of the present invention, as will be described.

Figure 1:
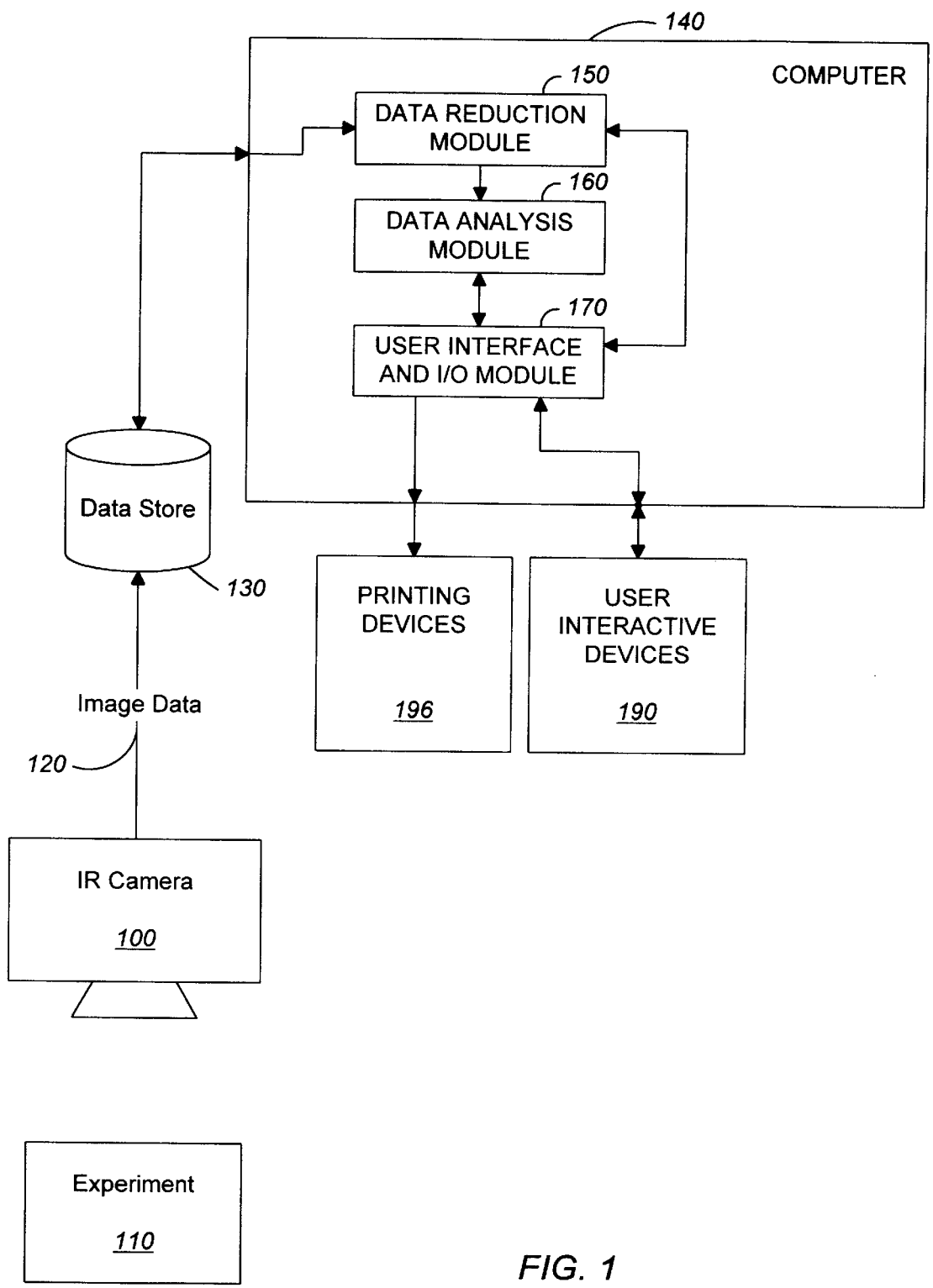
FIG. 1 is a block diagram of a data processing system showing an implementation of the invention.

Referring to FIG. 1, camera 100 observes experiment 110 and records one or more images representing experiment 110. In the exemplary system that will be described, camera 100 is a commercially available high performance infrared camera, such as the SE-IR CamIRa™, available from SE-IR Corporation of Goleta, Calif. Such cameras can be used to measure thermal properties such as radiant or photon emittance, existance, thermal flux and the like. Commercially available software, such as SE-IR Corporation's CamIRa™ software package, can be used to drive the camera's operations and to generate the images. Experiment 110 can be any experiment suitable for monitoring with camera 100. It can involve a single reaction vessel containing reagents or a single material deposited on a substrate within the field of view of camera 100. Alternatively, it can include a combinatorial array or "library" of distinct "members" (separate vessels of deposited materials), as will be discussed in more detail below.

Image data 120 generated by camera 100 is stored in data store 130 as an array of picture elements or "pixels," each of which is represented by a specific intensity or pixel value. Data processing system 140 retrieves image data 120 from data store 130; alternatively, data processing system 140 can receive image data 120 directly from camera 100 without intervening storage in data store 130. After retrieving the image data, data processing system 140 processes the image data in data reduction module 150 and data analysis module 160 either automatically or under user control. A user can interact with system 140 through user interface module 170. Data processing system 140 displays results through display or printing devices 190, 196.

Figure 2:
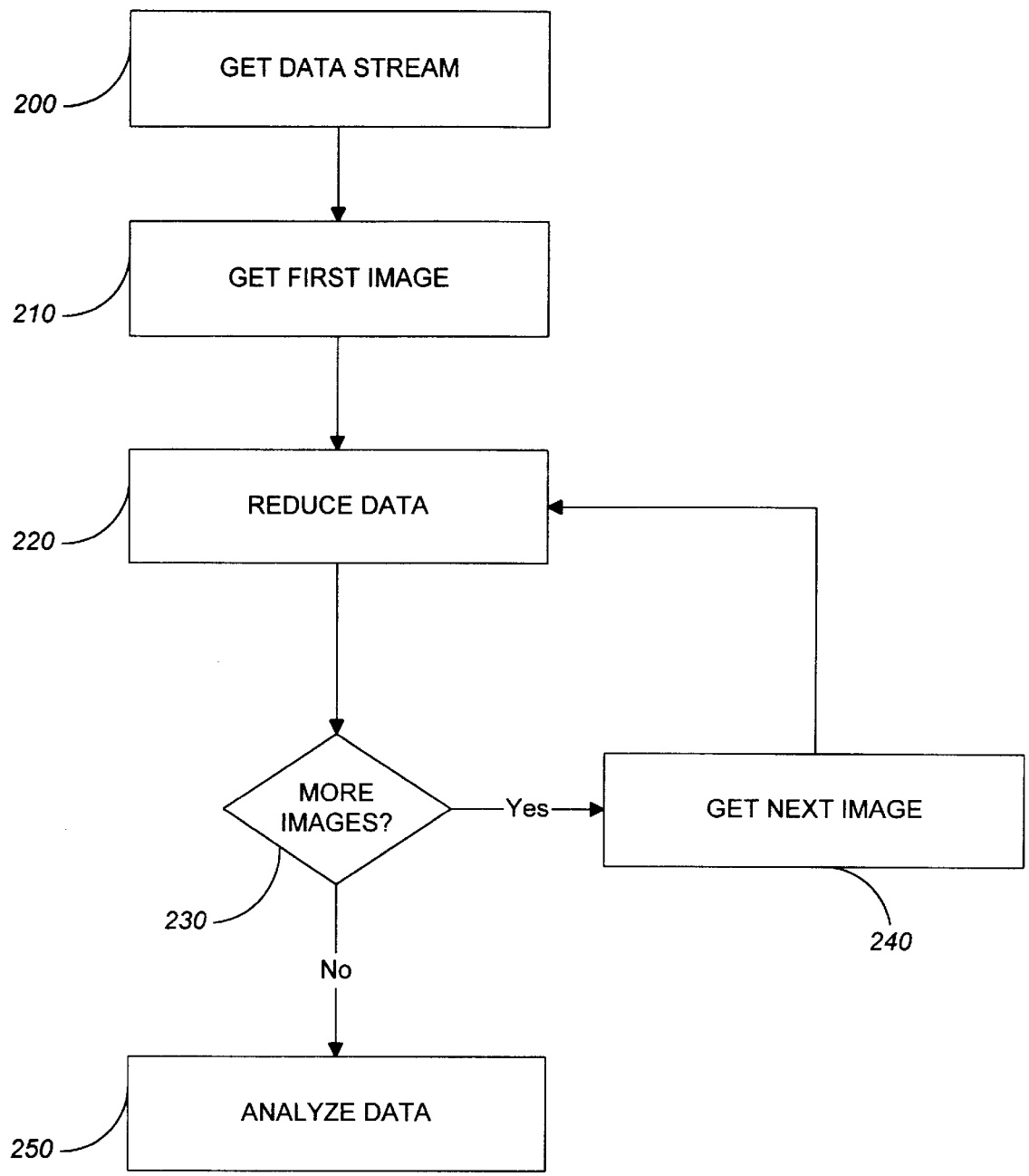
FIG. 2 is a flow diagram of a method of reducing a data stream.

As shown in FIG. 2, data reduction module 170. Data processing system 140 display results comprising a series of images from data store 130 or camera 100 (step 200). After getting the first image in the stream (step 210), data reduction module 150 reduces the data from that image, as will be described in further detail below (step 220). If additional images remain to be reduced (step 230), data reduction module 150 gets the next image (step 240) and reduces that image data (step 220). Data reduction module 150 provides the reduced data values to data analysis module 160 (step 250). Optionally, data processing system 140 stores the reduced data in data store 130.

Figure 3:
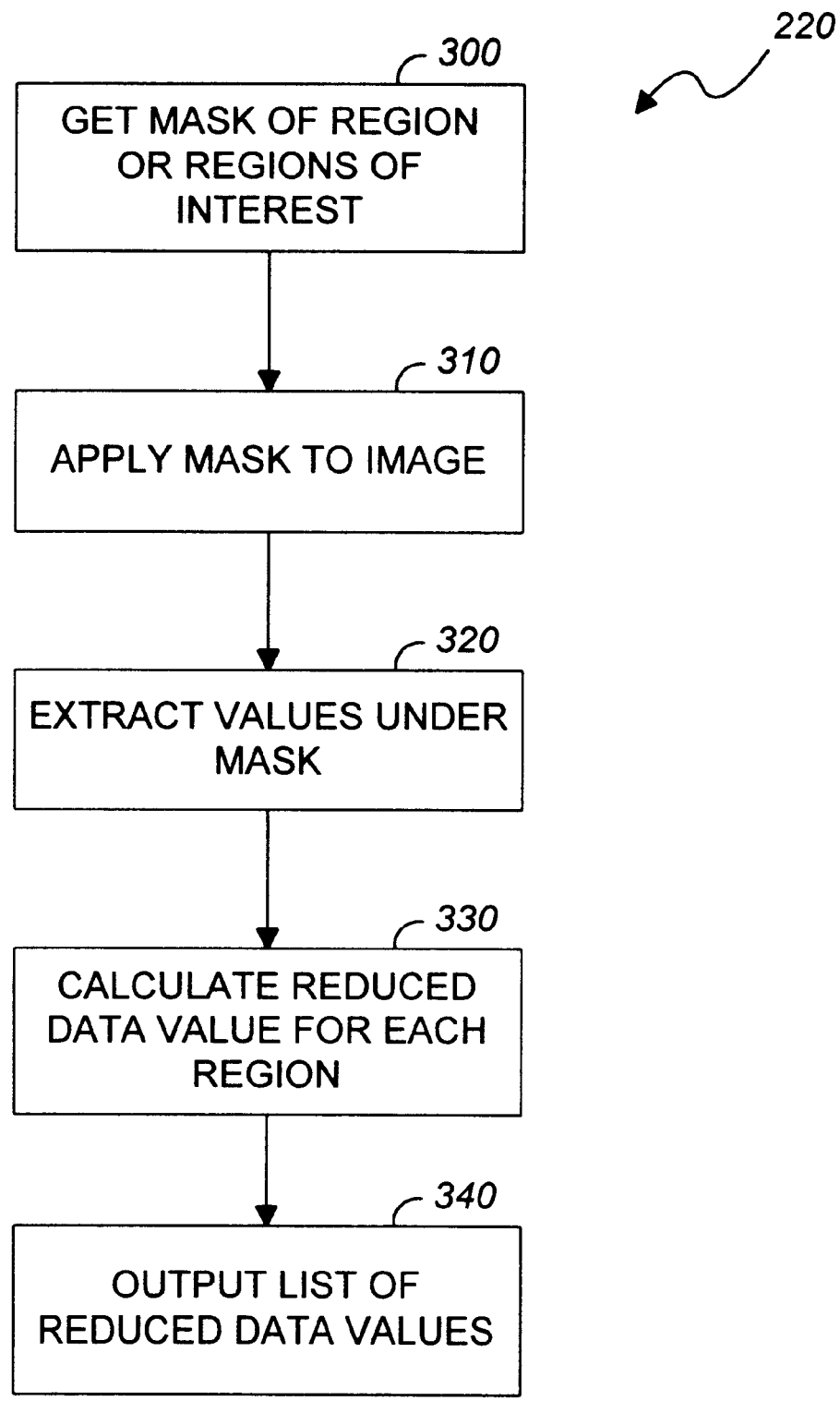
FIG. 3 is a flow diagram illustrating the method of FIG. 2 in more detail.

FIG. 3 describes data reduction step 220 in more detail. After receiving an image (step 210), data reduction module 150 obtains a user-defined mask identifying one or more regions of interest in the image (step 300). These regions may correspond, for example, to reaction vessel or materials that make up the elements of a combinatorial library used in experiment 110. Data reduction module 150 applies the mask to the image (step 310), and extract a value or values for each region of interest (step 320). Data reduction module 150 uses these values to calculate a reduced data value for each region of interest in the image (step 330). This reduced data value can be an average of intensity values recorded by camera 100 for points within a region of interest. It can also be an average change in intensity calculated by subtracting a reference point value, for example, a value measured for the region at an earlier time (e.g., in a previous image), a value measured for background noise or some other value (such as reflectance or base line). In other embodiments, the reduced data value can be calculated using other known statistical functions. Optionally, data reduction module 150 allows the user to select a desired function, for example by choosing from a menu of possible functions. Data reduction module 150 produces a list of reduced data values for the array of regions of interest, which is sent to data analysis module 160 (step 340). The list of reduced data values may also be stored for future use. Data reduction module 150 then determines whether additional images remain to be reduced (step 230).

Figure 4:
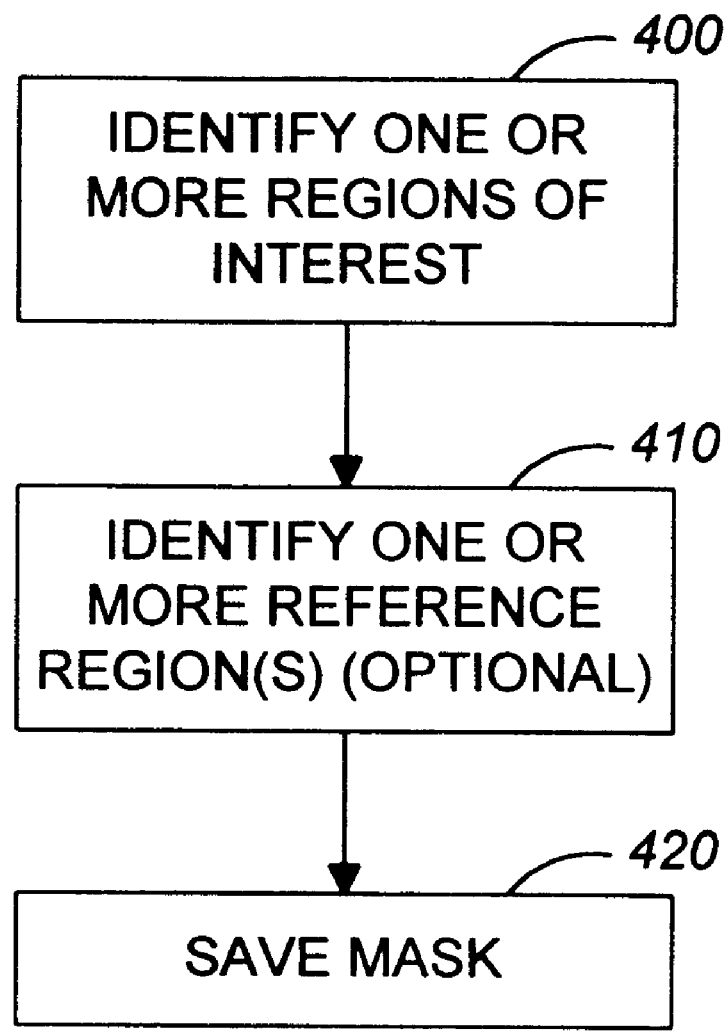
FIG. 4 is a flow diagram of a method of generating a mask.

The process of creating a mask is described in FIG. 4. Through user interface 170, the user identifies one or more regions of interest within an image (step 400). As discussed above, these regions will generally correspond to specific reaction vessels or materials that make up the elements of a combinatorial library monitored by camera 100. Optionally, the user can also specify one or more reference regions to which experimental data can be compared (step 410). Data processing system 140 saves the resulting mask in data store 130 for subsequent use during experiment 110, as well as for use during later experiments sharing a similar substrate geometry (step 420).

Figure 5A:
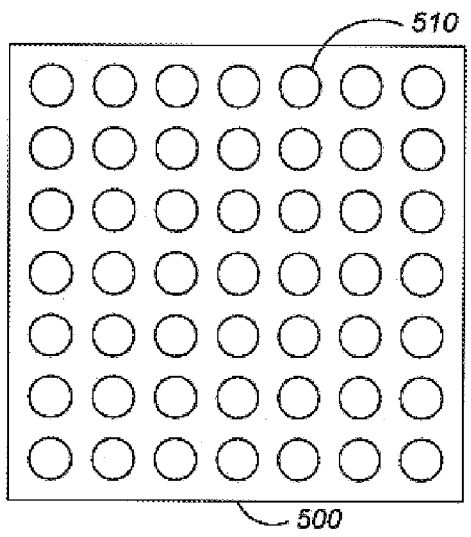
FIG. 5A is a diagram of a combinatorial library.
Figure 5C:
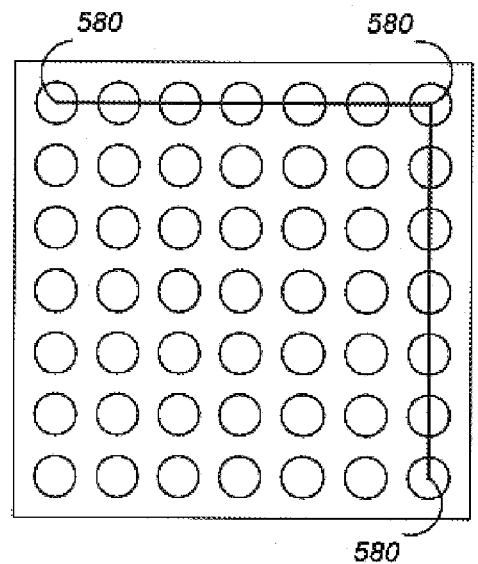
FIG. 5C is an illustration of selecting the corners of a mask.
Figure 5B:
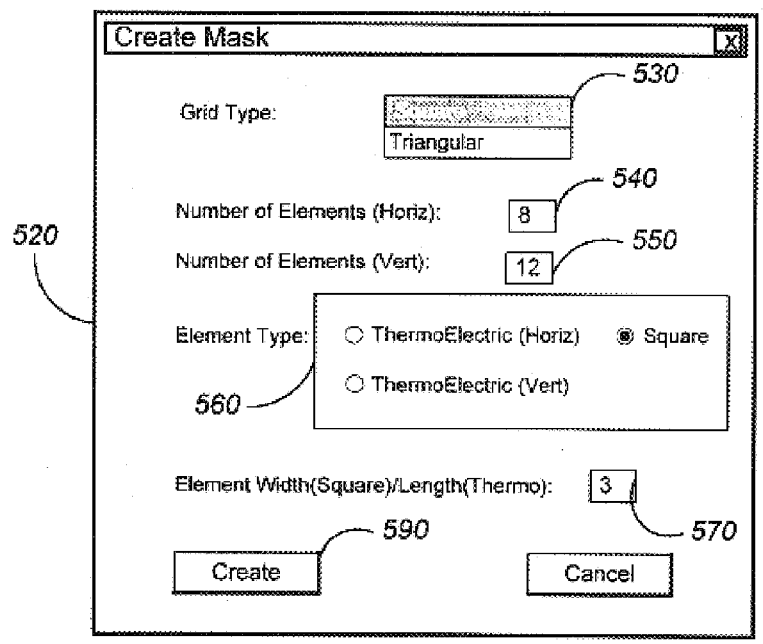
FIG. 5B is an illustration of a dialog window for creating a mask.

FIGS. 5A–5C detail the creation of a mask in one embodiment for an experiment involving a combinatorial library 500 of members 510 (FIG. 5A). User interface 170 displays "Create Mask" dialog window 520 (FIG. 5B). The user can select a grid type 530, as well as the number of horizontal and vertical members in the grid, 540 and 550, respectively. The user can also select a member type 560, according to the nature of experiment 110. In another embodiment, data reducing module 150 allows the user to define the shape of mask regions to correspond to any shape of library members 510, for example, through a user interface similar to those found in commercially available drawing and painting software known to those skilled in the art.

While FIG. 5B shows a "Create Mask" dialog for thermoelectric materials, the nature of the experiment is not a limiting feature for this invention as discussed below. The user can select a particular member length or width 570. After selecting the "Create" button, the user graphically specifies three corners 580 of the grid, clicks on the image and connecting lines are drawn (FIG. 5C). The elements of the grid can be moved as groups or individually to accommodate spacial irregularities in the physical substrate. Data reduction module 150 uses this information to create the mask.

Figure 6:
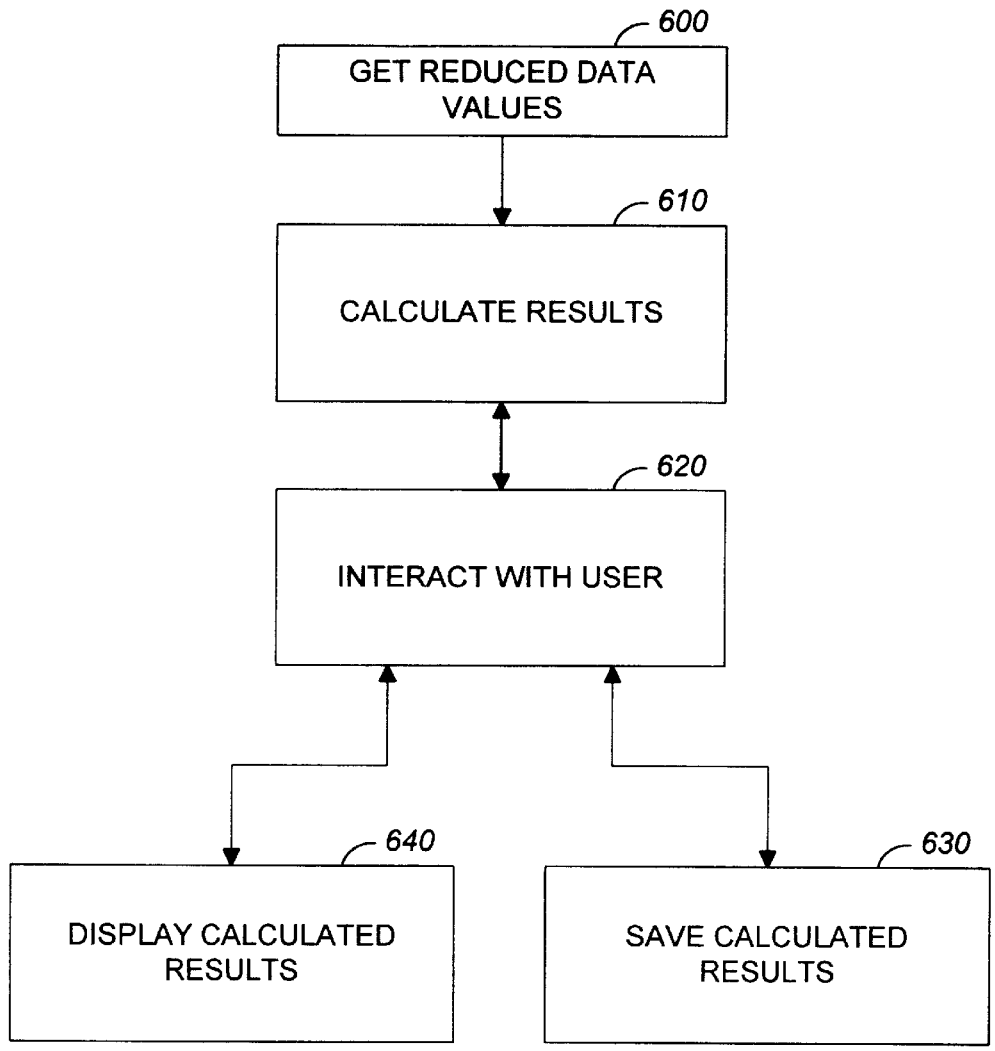
FIG. 6 is a flow diagram of a method of analyzing reduced data values and displaying calculated results.

As shown in FIG. 6, data analysis module 160 gets the list of reduced data values for each image from data reduction module 150 or data store 130 (step 600). Data analysis module 160 uses the values to calculate experimental results, including one or more figures of merit for each region of interest (step 610), as will be described in more detail below. The user can save the calculated results (steps 620 and 630), and can view the displayed results in a number of graphical formats (steps 620 and 640).

Figure 7:
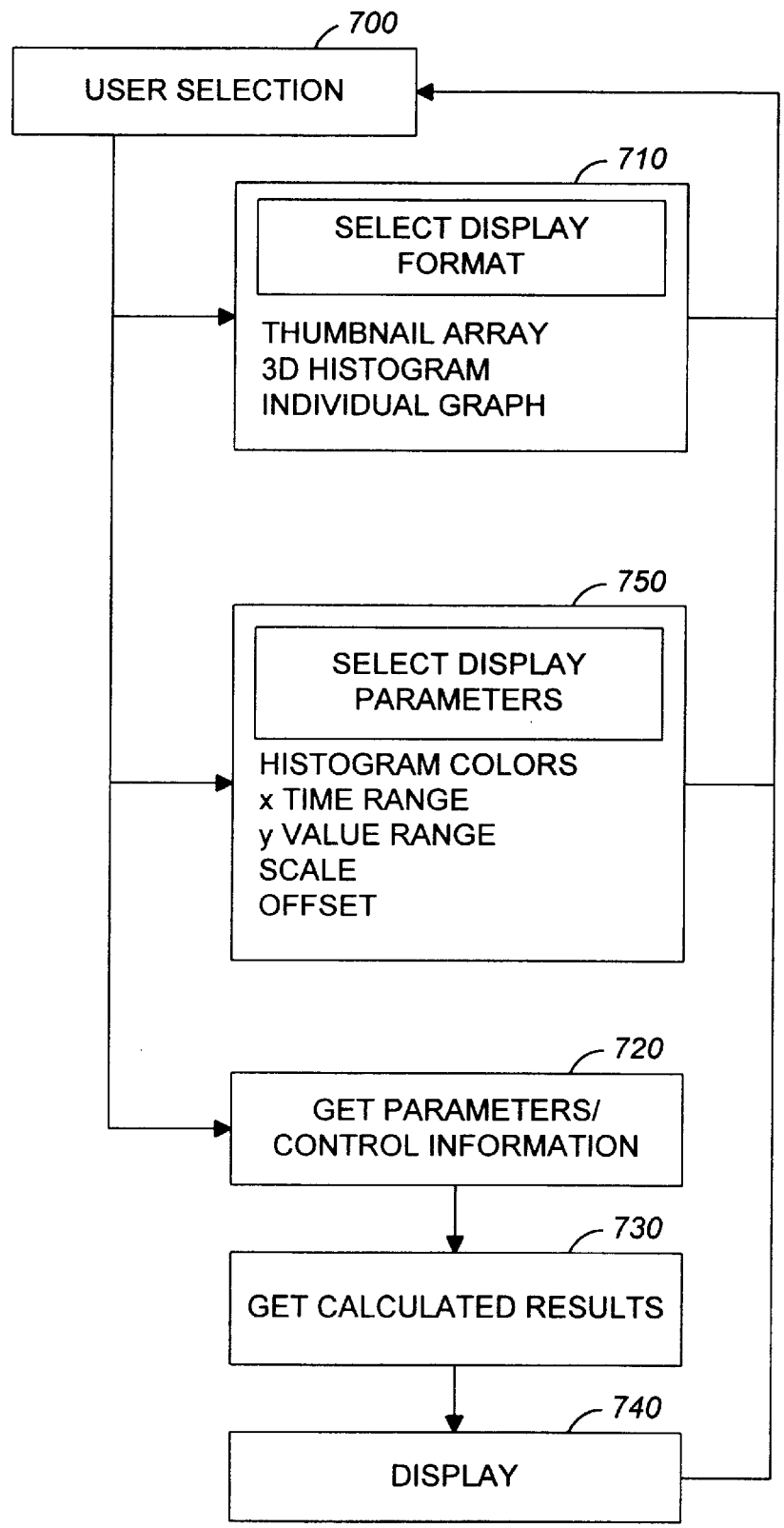
FIG. 7 is a flow diagram of a method of selecting display parameters and a display format.
Figure 8A:
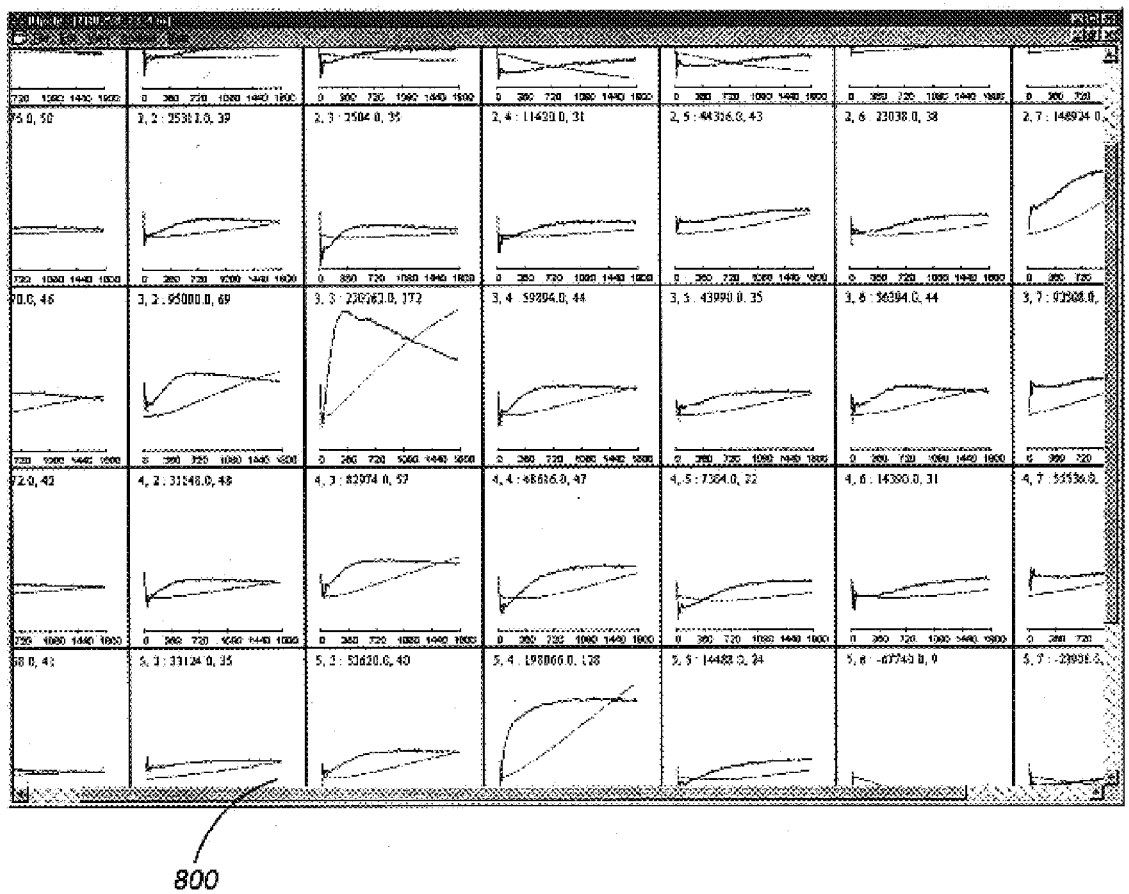
FIG. 8A–8C are illustration of formats for displaying experimental results.
Figure 8B:
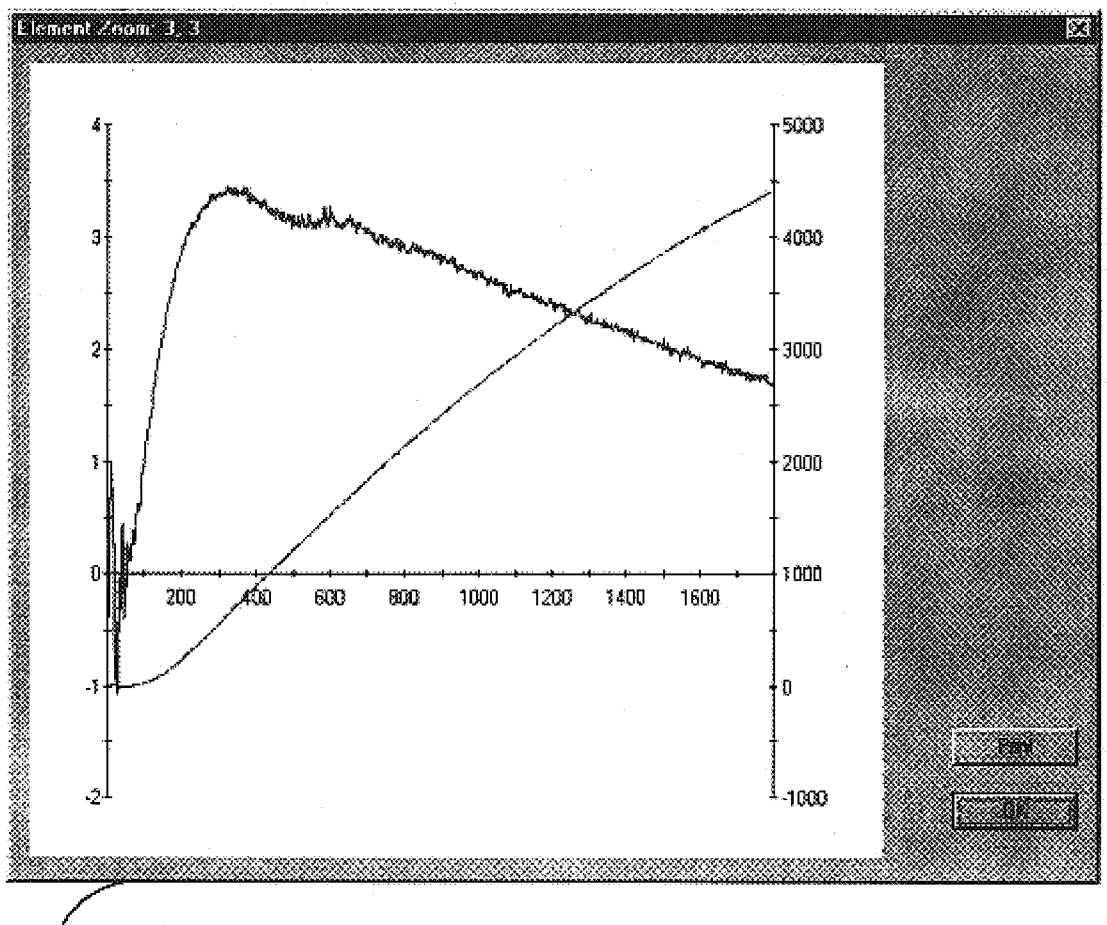
Figure 8C:
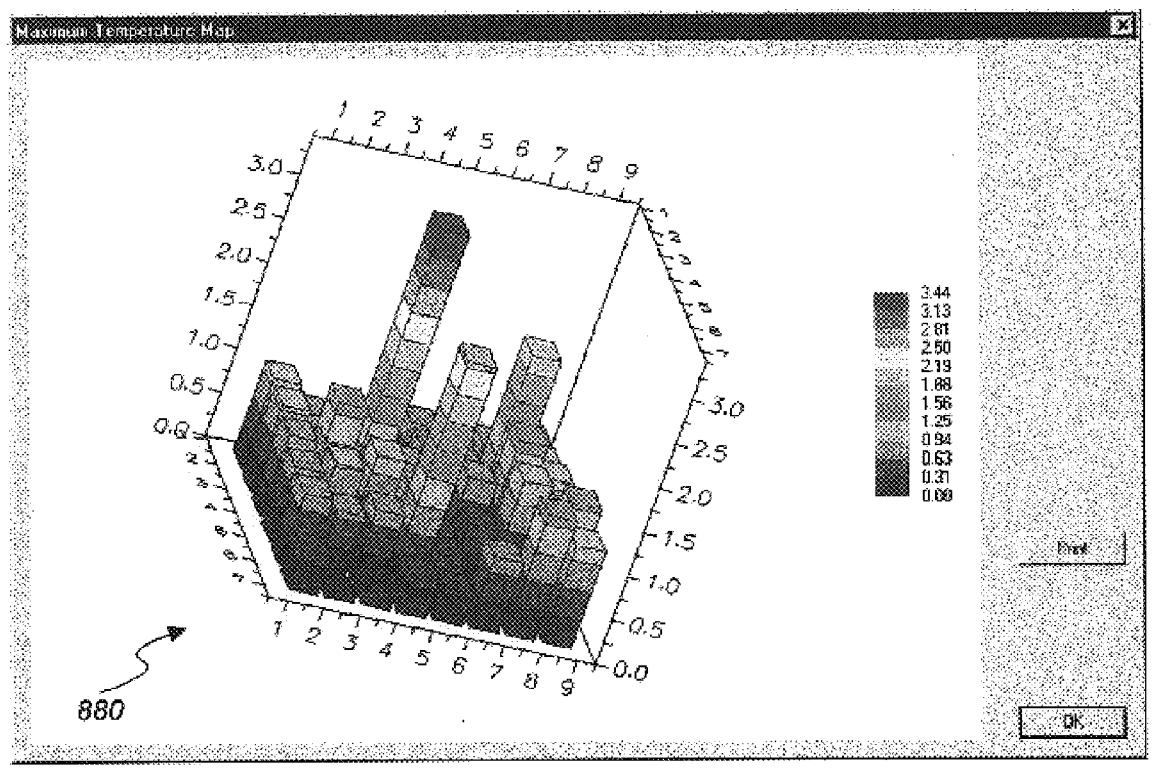

The user's interaction with data analysis module 160 (steps 620 through 640) is described in more detail in reference to FIG. 7. Through user interface 170, the user can select a variety of display options (step 700). These include a number of display formats (step 710) illustrated in FIGS. 8A–8C, such as an array of "thumbnail" graphs 800 plotting experimental data (for example, intensity versus time) for each region of interest a graph of experimental data for any selected region of interest (a "zoom-in" graph) 850, or a three-dimensional histogram 880 displaying a calculated value for each region of interest. Data analysis module retrieves display partners and control information (step 720) and gets the results calculated at step 610 (step 730). Data analysis module 160 displays the results in the selected display format (step 740). User selection step 700 also includes the option to choose display parameters (step 750). These include parameters such as histogram scale, range and colors, or time and value ranges for thumbnail or zoom-in graphs. By setting these parameters, the user can view experimental results over a specified time period, with the value at any specified time subtracted to show changes in temperature, or with a reference value (as described above) subtracted to remove background (or systematic) changes.

Figure 9:
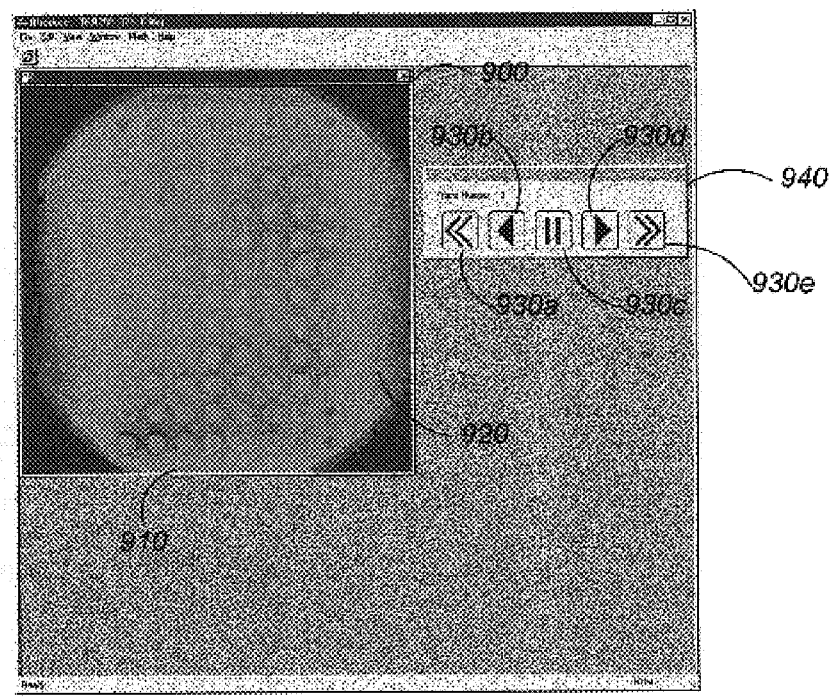
FIG. 9 is a window displaying images in data stream.

As shown in FIG. 9, the user can also view the original image or images recorded by camera 100. Window 900 displays an infrared image 910 of experiment 110, such as microtiter plate 920. Depending on the user-selected display parameters, different colors in infrared image 910 depict the range of heat emitted by objects within the field of camera 100. The user can navigate through the steam of images using buttons 930*a–e* provided in pane 940. Buttons 930*d* and 930*b* navigate forward or backward, respectively, by a single frame. Buttons 930*e* and 930*a* provide "fast forward" and "rewind" functions, respectively. In one embodiment, in "fast forward" mode data analysis module 160 and/or user interface module 170 determines the number of frames remaining in the stream of images and displays selected frames until it reaches the end of the stream. Similarly, in "rewind" mode, the number or preceding frames is determined and selected frames are displayed in reverse order until the beginning of the image stream is reached. Thus, for example, fast forward mode can display every tenth frame in a stream including 1000 frames, for a total of 100 frames displayed. Pane 940 also displays the frame number of the image displayed.

Data processing system 140 can be used to analyze material or chemical systems that lend themselves to characterization by IR thermography. Using IR thermography, the emittance (or existance) of an entire library of materials can be monitored with an infrared camera and the measured values can be used to derive a variety of thermodynamic properties associated with the materials. Commercial position sensitive systems such as infrared focal plane arrays can have a high sensitivity over a wide temperature range. Commercial infrared cameras incorporating such systems can acquire data at speeds up to 100 or more frames per second. In combination with such a system, data processing system 140 is particularly useful as a tool for quickly screening large numbers of materials for desirable thermodynamic characteristics. In one embodiment, data processing system 140 receives images at a rate of 12 to 20 frames per second and reduces the data by averaging values for each frame to obtain the equivalent of one averaged frame of data per second, thereby increasing the signal to noise ratio of the experimental results.

Depending on the process being monitored, different data acquisition rates—for example, rates of about 1,6, 12 or 20 frames per second—provide a data stream suitable for deriving a reaction profile sufficient to track many chemical reactions, material transformations and thermal diffusion transients. Higher data acquisition rates are useful in characterizing processes requiring a relatively high degree of resolution. For example, metal compositions can be characterized based on the range of temperatures at which melting occurs. For many metal compositions, melting begins at one temperature and continues until the material reaches a higher temperature. The first temperature, below which the entire sample is in a solid phase, is known as the solidus temperature; the second, above which the entire sample is in a liquid phase, is known as the liquidus temperature. To identify eutectic compositions—those in which the solidus temperature and liquidus temperature are equal—it is useful to screen an array of metals covering a range of compositions for those having the lowest liquidus temperature. By rapidly heating such an array, it is possible to exceed a composition's solidus temperature without the onset of melting due to slow diffusion in the solid state. If heating is sufficiently rapid—for example at 20° to 60° C. per second—it is possible to reach the liquidus temperature without melting, at which point the entire sample quickly melts. Data acquisition at speeds of 18 to 20 frames per second are sufficient to resolve such rapid thermodynamic changes.

The features and advantages of the invention can be appreciated from a description of its application to a particular implementation in the field of infrared thermography—the characterization of thermoelectric materials.

Thermoelectric Materials

Thermoelectric devices are solid state devices that pump heat from one junction to another when subjected to an electric current, a phenomenon known as the Peltier effect. Thermoelectric materials are characterized by a number of physical parameters including the thermal conductivity $\kappa$, the electrical conductivity $\sigma$, the Seebeck coefficient S, the Hall coefficient $R_H$, the charge carrier mobility $\mu$, the device operating temperature T, the change carrier effective mass m*, and the band gap $E_g$. An estimate of the thermoelectric device efficiency for pumping heat relative to the heat lost due to the electrical resistivity is the thermoelectric figure of merit defined by:

$$ZT = \frac{S^2 \sigma T}{\kappa}$$

Figure 10:
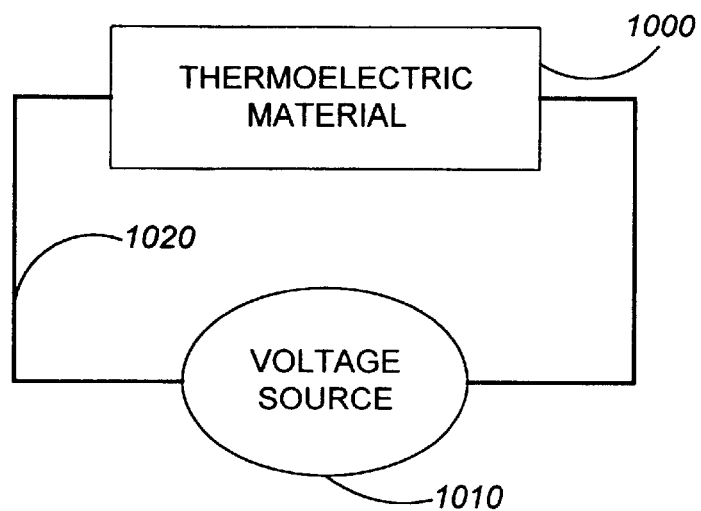
FIG. 10 is a schematic diagram of a thermoelectric device.

FIG. 10 illustrates a model thermoelectric device constructed from a thermoelectric material 1000 connected to voltage source 1010 with voltage wires 1020 made of a high conductivity metal. Under steady state or adiabatic conditions, the heat pumped by the Peltier effect will be equal to the heat carried by the thermal conduction, which leads to the following relationship for the thermoelectric figure of merit:

$$ZT = \frac{Q_{Peltier}}{Q_{Joule}} = \frac{P_{Peltier}}{P_{Joule}}$$

$Q_{Peltier}$ and $Q_{Joule}$ are the amount of heat transported by the Peltier effect and the amount of energy lost to Joule heating, respectively; $P_{Peltier}$ and $P_{Joule}$ are each the corresponding power (heat per unit time). The expression for the total power dissipated in the device is given by the sum of the thermoelectric (Peltier) and Joule components;

$$P = P_{Joule} + P_{Peltier} = \frac{V^2}{R} + \Pi \frac{V}{R}$$

where the first term is the powder dissipated by Joule effects ($P_{Joule}$) and the second term is the contribution from the Peltier component ($P_{Peltier}$); R is the electrical resistance of the circuit and Π is the Peltier coefficient of the thermoelectric material measured relative to the material that makes up the voltage contacts. Application of an oscillatory voltage at a reference frequency $\omega_0$, such as $V(t)=V_0\cos(\omega_0 t)$, causes the Joule term to oscillate at twice the reference frequency ($2\omega_0$) due to the voltage being squared, while the Peltier term is linear in voltage and is observed at the reference frequency $\omega_0$. Measurement of the power dissipated at the junction between the voltage contact and the thermoelectric material as a function of time, P(t), followed by a Fourier transform to power as a function of frequency, P($\omega$), allows the contribution due to Joule effects to be distinguished from (and compared to) the contribution due to Peltier effects. The ratio of the two amplitudes $P(\omega_0)/P(2\omega_0)$ is the thermoelectric figure of merit ZT.

The present invention provides a fast and efficient screen for the identification of thermoelectric materials in a combinatorial library of candidate materials, as well as an analytical tool for characterizing such materials by determining the thermoelectric figure of merit. Suitable libraries can be created using techniques such as those described in U.S. Pat. No. 5,776,359, which is incorporated herein by reference in its entirety.

Figure 11:
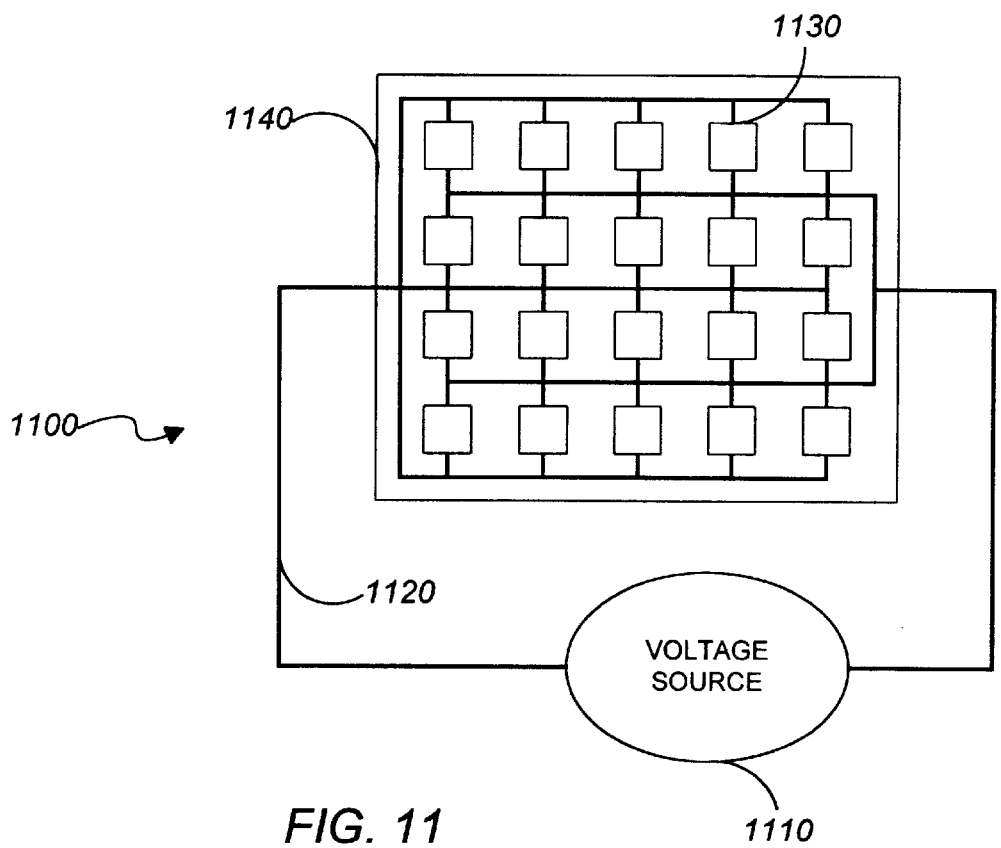
FIG. 11 is a schematic diagram of a thermoelectric device including a combinatorial array of thermoelectric materials.

As shown in FIG. 11, in combinatorial thermoelectric device 1100, voltage source 1110 applies a parallel voltage through voltage wires 1120 to all members 1130 in a combinatorial library 1140. Library 1140 is made from a material with low thermal conductance, such as 25 to 50 micron thick polyimide sheets to minimize heat lost to the substrate holding elements 1130; for the same reason, library 1140 is maintained in an evacuated environment to minimize heat lost to the surroundings. To maintain adiabatic conditions, the voltage applied by voltage source 1110 is kept as small as possible, with reference frequencies typically being on the order of 0.1 Hz or less. Voltage wires 1120 are made of a high conductivity metal such as Ag, Au, Cr, Ta, or Cu to maintain good electrical contact and because their Peltier coefficients are low relative to those found in semiconducting materials.

As discussed more generally above, data reduction module 150 obtains a series of images of thermoelectric device 1100 from infrared camera 100. Data reduction module 150 generates reduced data values as described above, and provides those values to data analysis module 160.

Figure 12A:
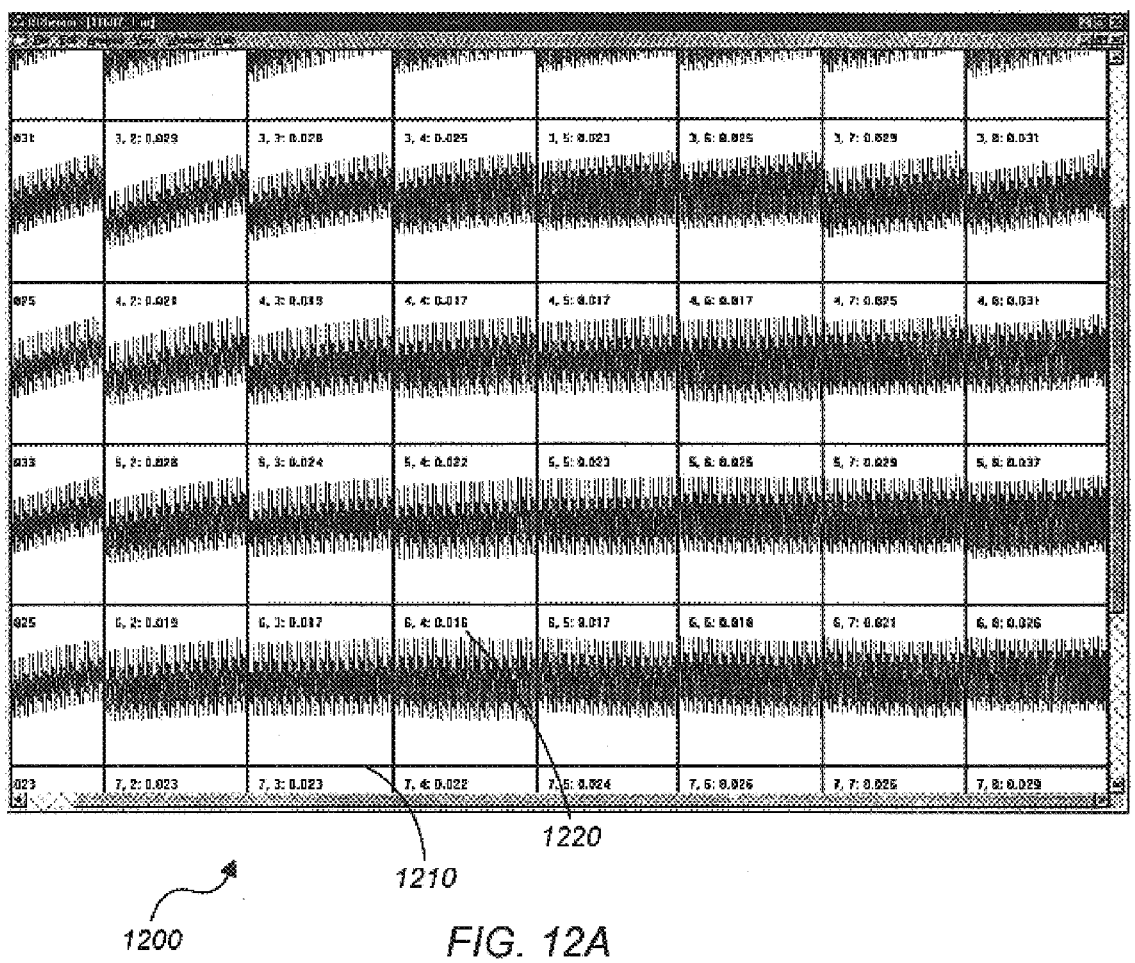
FIGS. 12A–12B are illustrations of display formats for a combinatorial thermoelectric materials experiment.
Figure 12B:
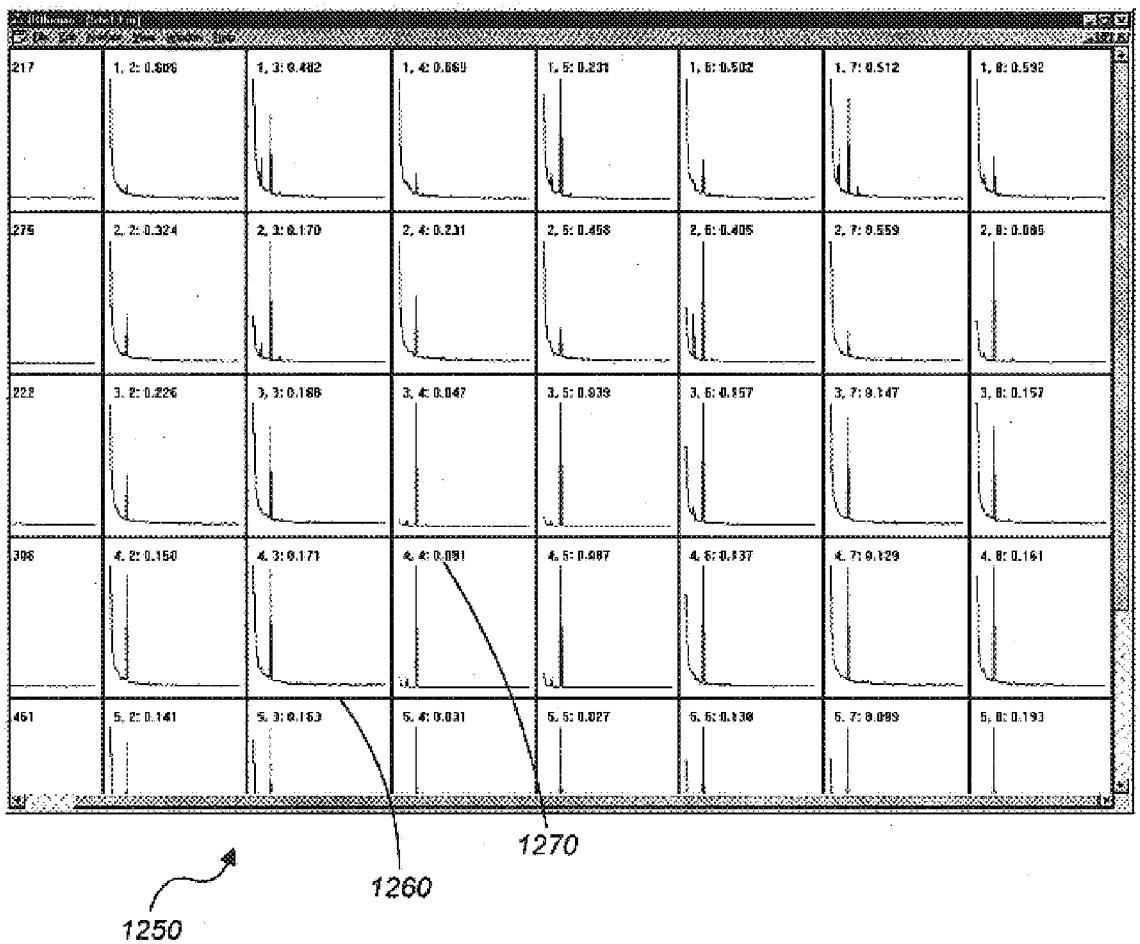

With these reduced data values, data analysis module 160 calculates the intensity as a function of frequency for each region of interest using fast Fourier transform. As shown in FIGS. 12A and 12B, the user can view the data geographically, in either the time domain 1200 or the frequency domain 1250. Data analysis module 160 uses the frequency data to calculate the thermoelectric figure of merit for each region of interest as described above. The figure of merit (1220, 1270) is displayed in thumbnail graphs 1210 and 1260. The user can also view a three dimensional histogram displaying the figure of merit for each region of interest, as described above.

Chemical Transformations

Figure 13:
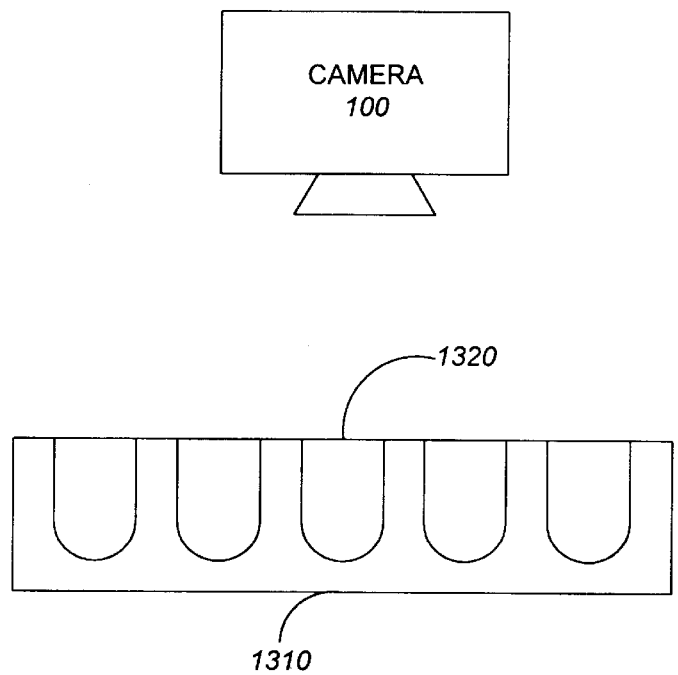
FIG. 13 is a schematic diagram of a combinatorial experiment to monitor heats of reaction.

Data processing system 140 can also be used to monitor the progress of chemical reactions or transformations. In many embodiments, the reaction is a catalytic reaction and catalyst activity is being determined, which is the example described below. Referring to FIG. 13, in this application an infrared camera 100 monitors emittance associated with heat evolution or absorption or with a compound or chemical's disappearance from or appearance in a combinatorial library 1310 under various external conditions such as temperature and gas flow. For example, if a solid catalyst library and its surrounding support in a two-dimensional library are exposed to a reactant, a measurable heating of the surroundings may occur depending on the activity of the chemical process. Such libraries can be generated using techniques such as those disclosed in U.S. application Ser. No. 08/898,715, filed Jul. 22, 1997, or Ser. No. 09/227,558, filed Jan. 8, 1999, which are both incorporated herein by reference in their entirety. In the case of a catalyst, the activity of the catalyst correlates to the energy released or absorbed as heat during the chemical reaction between the catalyst and the exchange gas. In a combinatorial library 1310, members 1320 are nearly identical in thermal mass, so measurements of the heat evolved by one element in the library relative to others within the library can be used to characterize the chemical processes induced by these materials.

Figure 14:
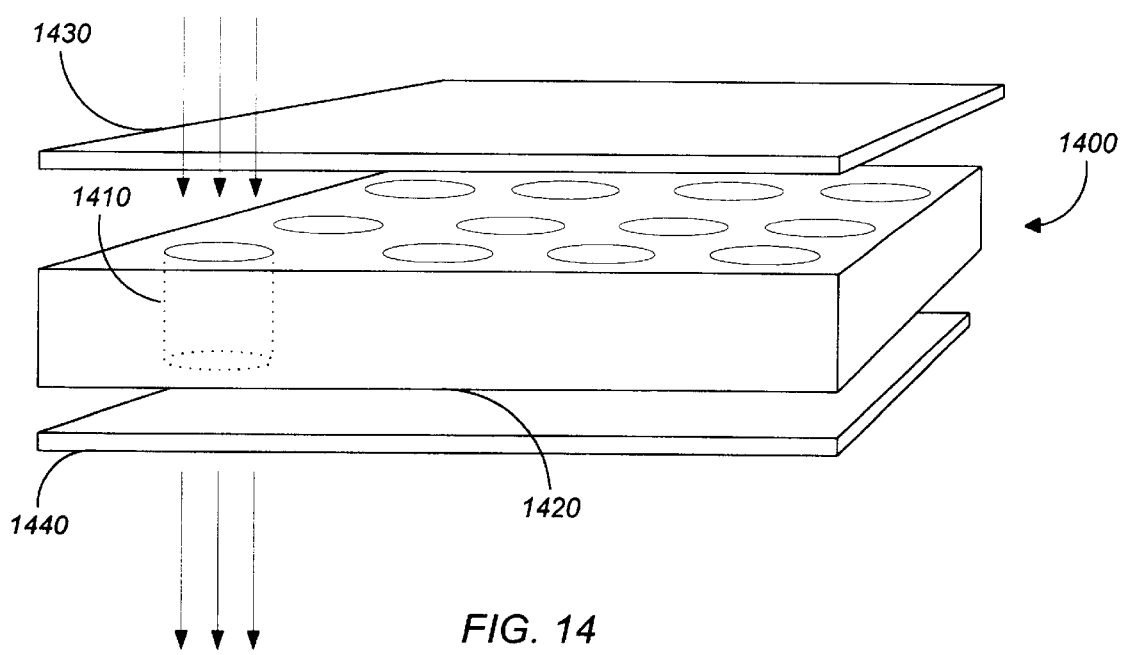
FIG. 14 is a diagram illustrating the combinatorial library of FIG. 13 in more detail.

FIG. 14 illustrates a two-dimensional library 1400 of materials useful in this embodiment. The individual library members are reaction wells 1410 in a substrate 1420. Substrate 1420 is placed within a sealed reaction chamber which is pressurized with the relevant gas. Windows 1430 and 1440 are made of an infrared transparent medium (such as sapphire, antireflection coated silicon, BaF$_2$, CaF$_2$ or NaCl) capable of maintaining the pressurized gas inside the chamber. Since window 1430 and 1440 are transparent to infrared radiation, thermal imaging techniques can be used to monitor the heat of reaction of each library element under various external conditions.

Measuring the heat generated by a catalytic transformation is a powerful technique for rapidly screening catalyst efficacy. For condensed phase reactions, there is direct thermal contact between the catalyst, products, and solvent. Thus, the library can be directly imaged and the emissivity of the samples will be roughly that of the pure solvent, allowing direct comparison of the members in a library. In cases where emissivity differences exist between materials in the library, direct comparison of library members is more complicated, but the experimental results are still useful in screening for raw catalyst activity. Differences in emissivity may also be dealt with by imaging the library through a material (such as graphite). This technique is particularly useful for screening gas phase reactions, where the catalysts is mounted on a support and large emissivity differences are common. In this case, the reaction can be monitored from the backside of the catalyst support.

In a typical experiment, a library is loaded into a sample chamber with an IR transparent window and the entire system is allowed to come to thermal equilibrium. The sample is monitored with camera 100 to establish a background reading, and the chamber is pressurized with a reactant gas. The sample is monitored by camera 100 over the course of the catalytic reaction, for example, for about one hour. The resultant data is analyzed as will be described below. The change in emittance is directly proportional to the catalytic activity of the library member.

As discussed more generally above, data reduction module 150 obtains a series of images of library 1400 from infrared camera 100. Data reduction module 150 generates reduced data values as described above, and furnishes those values to data analysis module 160.

With these reduced data values, data analysis module 160 calculates the integral of intensity (proportional to the total conversion of starting material). As described above, the user can view the data in the form of an array of graphs 800 of intensity versus time and integral of intensity versus time. Each thumbnail graph also depicts two figures of merit for each region of interest—the total integrated intensity and the maximum intensity for the element. The user can also view a three dimensional histogram displaying either figure of merit for each region of interest.

Metals

Data processing system can also be used to characterize melting points of metals or other materials (e.g., composite materials) using infrared imaging. In this application, an infrared camera 100 is used to monitor a library whose members include a series of metals or other materials. Suitable libraries can be generated using techniques such as those described in U.S. Pat. No. 5,776,359, which is incorporated herein by reference in its entirety. Camera 100 measures intensities that are a function of temperature and emissivity of each member. Changes in the structure and bonding of a chemical composition during a transition from one thermodynamic phase to another result in a change in the composition's emissivity. During a phase transition the temperature of a library member may change or the rate of temperature change may increase or decrease. The thermodynamics of given material's phase transition can be characterized by comparing the emissivity changes over a given temperature range with that of a standard material having a constant emissivity in the relevant temperature range.

The infrared camera 100 monitors the intensity from every library member in parallel and compares it to the intensity of a known standard material within the field of view of the camera (which may be the substrate holding the library) and subjected to the same physical conditions as the library members. In this way, complicated phase relationships are measured for large libraries of materials by heating or cooling the library and deriving changes in the emissivity.

Figure 15:
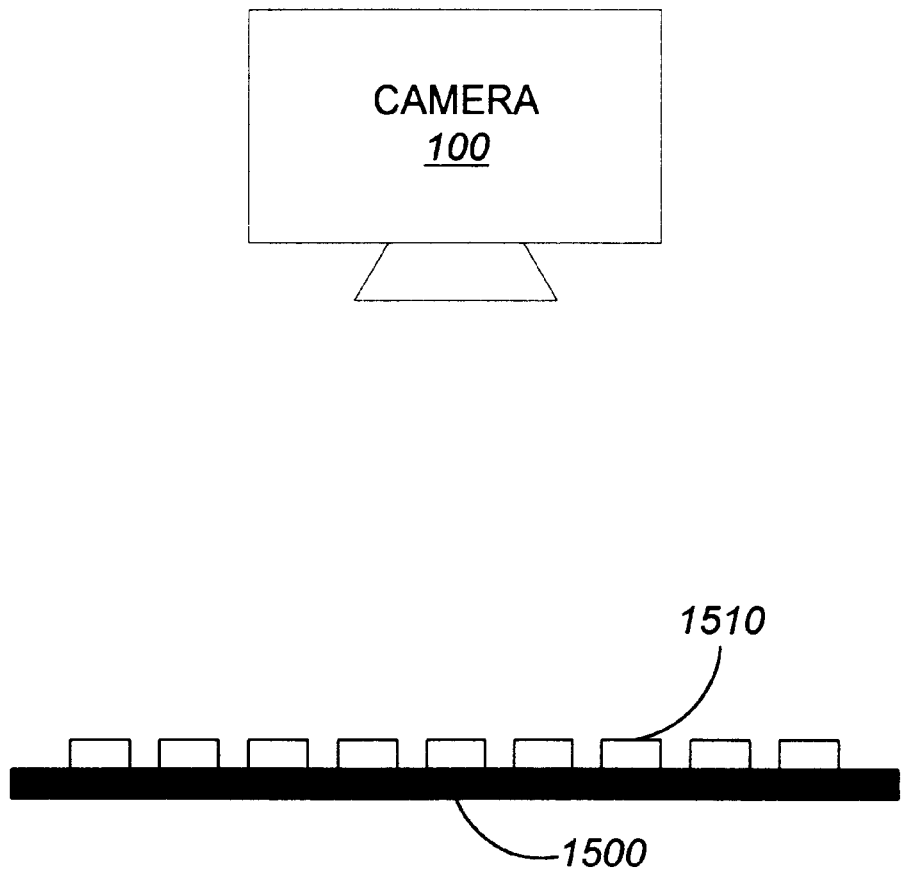
FIG. 15 is a diagram of a combinatorial experiment to determine phase transition points of a library of materials.

Referring to FIG. 15, as discussed more generally above, in this embodiment camera 100 records infrared images of library 1500, including library members 1510, as the temperature is varied over a range of interest. Data reduction module 150 obtains a series of images of library 1500 and generates reduced data values as described above. Data reduction module 150 furnishes those values to data analysis module 160.

Using these reduced data values, data analysis module 160 calculates the relative emissivity of each library member as compared to the standard. After smoothing the data, data analysis module 160 calculates the derivative of the ratio of library member emissivity to standard. The maximum rate of change occurs a the material's melting point which here is the figure of merit. As described above, the user can view the experimental results as an array of thumbnail graphs 800 depicting a plot of intensity versus time for a given library member, intensity versus time for the standard sample (which may be the substrate) and a plot that is a ratio of the first two plots. The user can also view a reduced plot of melting point as a function of library member. The figure of merit—the melting point calculated as described above—is also displayed. As described above, the user can also veiw the data as a three dimensional histogram displaying either figure of merit for each library element.

The invention can be implemented in digital electronic circuitry, or in computer hardware, firmware, software, or in combinations of them. Apparatus of the invention can be implemented in a computer program product tangibly embodied in a machine-readable storage device for execution by a programmable processor; and method steps of the invention can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Data can also be temporarily stored in volatile memory. Any of the foregoing can be supplemented by, or incorporated in, ASICs (application-specific integrated circuits).

To provide for interaction with a user, the invention can be implemented on a computer system having a display device such as a monitor or LCD screen for displaying information to the user and a keyboard and a pointing device such as a mouse or a trackball by which the user can provide input to the computer system. The computer system can be programmed to provide a graphical user interface through which computer programs interact with users.

Figure 16:
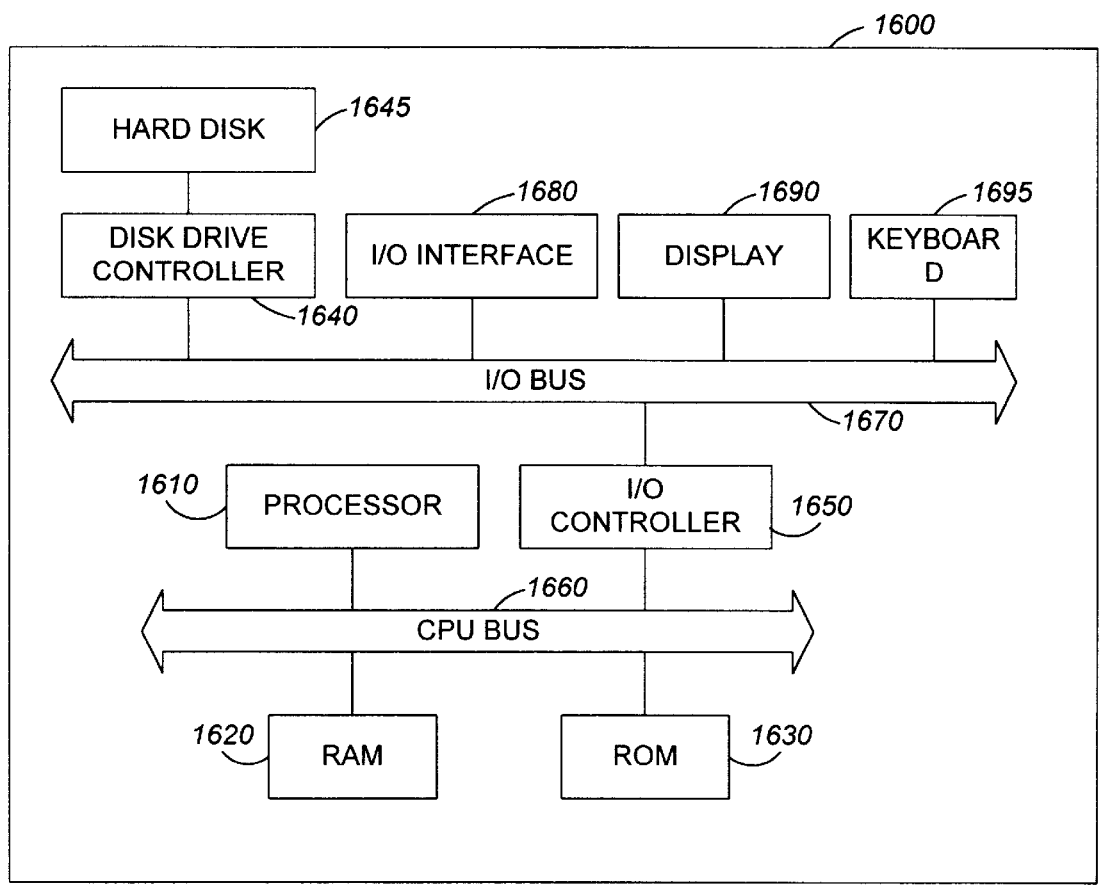
FIG. 16 is a schematic diagram of a computer platform suitable for implementing the data processing system of the invention.

An example of one such type of computer is shown in FIG. 16, which shows a block diagram of a programmable processing system (system) 1600 suitable for implementing or performing the apparatus or methods of the invention. The system 1600 includes a processor 1610, a random access memory (RAM) 1620, a program memory 1630 (for example, a writable read-only memory (ROM) such as a flash (ROM), a hard drive controller 1640, and an input/output (I/O) controller 1650 coupled by a processor (CPU) bus 1660. The system 1600 can be preprogrammed, in ROM, for example, or it can be programmed (and reprogrammed) by loading a program from another source (for example, from a floppy disk, a CD-ROM, or another computer).

The hard drive controller 1640 is coupled to a hard disk 1645 suitable for storing executable computer programs, including programs embodying the present invention, and data including the images, masks, reduced data values and calculated results used in and generated by the invention.

The I/O controller 1650 is coupled by means of an I/O bus 1670 to an I/O interface 1680. The I/O interface 1680 receives and transmits data (e.g., stills, pictures, movies, and animations for importing into a composition) in analog or digital form over communication links such as a serial link, local area network, wireless link, and parallel link.

Also coupled to the I/O bus 1670 is a display 1690 and a keyboard 1695. Alternatively, separate connections (separate buses) can be used for the I/O interface 1670, display 1690 and keyboard 1695.

The invention has been described in terms of particular embodiments. Other embodiments are within the scope of the following claims. For example, the invention has been described as being implemented in a number of different embodiments, each intended to monitor, analyze and display data for a different experiment. Alternatively, a number of different applications can be implemented in a single system, for example, where data processing system 140 includes multiple versions of data analysis module 140, each designed to analyze and display data from a different type of experiment. Also, data structures other than the ones mentioned above can be used in storing and processing data. For example, mask and image information can be encapsulated in objects and stored in an object oriented database. In addition, the steps of the invention can be performed in a different order and still achieve desirable results.

What is claimed is:

1. A computer program on a computer-readable medium for evaluating a corobinatorial library, the program comprising instructions to:
   receive a stream of data comprising a series of images of a combinatorial library, the combinatorial library including a plurality of members, each member being associated with a location in the combinatorial library;
   receive user input identifying a plurality of regions of interest, each region corresponding to a location in each of the series of images and to a location in the combinatorial library;
   determine a series of values for one or more regions of interest, the series of values for each of the one or more regions comprising a value for each of the images; and
   calculate from each series of values for the one or more regions a figure of merit for the library member at the corresponding library location.

2. The computer program of claim 1, wherein each region of interest corresponds to a plurality of pixels in each image and the series of values for a region of interest comprises an average value for each of the corresponding plurality of pixels in each of the images.

3. The computer program of claim 2, wherein the stream of data comprises a series of images generated at a frequency of greater than about 1 frame per second.

4. The computer program of claim 2, wherein the stream of data comprises a series of images generated at a frequency of greater than about 6 frames per second.

5. The computer program of claim 2, wherein the stream of data comprises a series of images generated at a frequency of greater than about 12 frames per second.

6. The computer program of claim 2, wherein the stream of data comprises a series of images generated at a frequency of greater than about 20 frames per second.

7. The computer program of claim 2, further comprising instructions to display a graphical representation of the figures of merit.

8. The computer program of claim 7, wherein the graphical representation comprises a histogram.

9. The computer program of claim 1, wherein the series of images is captured from a first time during a combinatorial experiment to a second time during the combinatorial experiment.

10. The computer program of claim 1, wherein the series of images comprises a series of infrared images.

11. The computer program of claim 10, wherein the figure of merit comprises an emittance change for a library member.

12. The computer program of claim 10, wherein the figure of merit comprises a phase transition point for a library member.

13. The computer program of claim 10, wherein the figure of merit comprises a thermoelectric figure of merit for a library member.

14. The computer program of claim 1, wherein the instructions to identify a plurality of regions of interest comprise instructions to receive a first user input identifying one or more regions of interest, each region having a user-defined shape, the computer program further comprising instructions to receive a second user input defining a computation for determining a series of values for each of the one or more regions of interest.

15. The computer program of claim 14, wherein the instructions to determine a series of values for each of the one or more regions of interest comprise instructions to compute each valve in each series in accordance with the second user input.

16. The computer program of claim 15, wherein the computation is an average for a group of pixels corresponding to a region of interest.

17. The computer program of claim 1, wherein the plurality of regions of interest is identified after the series of images has been captured.

18. A computer program on a computer-readable medium for evaluating a corobinatorial library, the program comprising instructions to:
   receive a stream of data comprising a series of images of a combinatorial library, the combinatorial library including a plurality of members, each member being associated with a location in the combinatorial library;
   receive a first user input identifying one or more regions of interest, each region having a user-defined shape and each region corresponding to a location in each of the series of images and to a location in the combinatorial library;
   receive a second user input defining a computation for determining a series of values for each of the one or more regions of interest, each series of values comprising a value for each of the images; and
   determine a series of values for each of the one or more regions of interest, each value in each series being computed in accordance with the second user input.

19. The computer program of claim 18, further comprising instructions to calculate from each series of values for the one or more regions a figure of merit for the library member at the corresponding library location.

20. A computer program for evaluating a combinatorial chemical experiment, the program comprising instructions to:
   receives a series of images of a combinatorial library, the library including a plurality of members, each member being associated with a location in the combinatorial library, the series of images being captured from a first time during the experiment to a second time during the experiment;

after the series of images has been received, receive user input identifying a plurality of regions of interest, each region corresponding to a location in each of the series of images and to a location in the combinatorial library; and determine a series of values for one or more regions of interest, the series of values for each of the one or more regions comprising a value for each of the images.

21. The computer program of claim 20, further comprising instructions to calculate from each series of values for the one or more regions a figure of merit for a library member at the corresponding library location.

22. The computer program of claim 21, further comprising instructions to display a graphical representation of each figure of merit.

23. A method for evaluating a combinatorial library, the method comprising:

receiving a stream of data comprising a series of images of a combinatorial library, the combinatorial library including a plurality of members, each member being associated with a location in the combinatorial library;

receive user input identifying a plurality of regions of interest, each region coresponding to a location in each of the series of images and to a location in the combinatorial library;

determining a series of values for one or more regions of interest, the series of values for each of the one or more regions comprising a value for each of the images; and calculating for each series of values for the one or more regions a figure of merit for the library member at the corresponding library location.

24. The method of claim 23, wherein each region of interest corresponds to a plurality of pixels in each image and the series of values for a region of interest comprises an average value for each of the corresponding plurality of pixels in each of the images.

25. The method of claim 24, wherein the stream of data comprises a series of images generated at a frequency of greater than about 1 frame per second.

26. The method of claim 24, wherein the stream of data comprises a series of images generated at a frequency of greater than about 6 frames per second.

27. The method of claim 24, wherein the stream of data comprises a series of images generated at a frequency of greater than about 12 frames per second.

28. The method of claim 24, wherein the stream of data comprises a series of images generated at a frequency of greater than about 20 frames per second.

29. The method of claim 24, further comprising displaying a graphical representation of the figures of merit.

30. The method of claim 29, wherein the graphical representation comprises a histogram.

31. The method of claim 23, wherein the series of images is captured from a first time during a combinatorial experiment to a second time during the combinatorial experiment.

32. The method of claim 31, wherein the series of images comprises a series of infrared images.

33. The method of claim 32, wherein the figure of merit comprises an emittance change for a library member.

34. The method of claim 32, wherein the figure of merit comprises a phase transition point for a library member.

35. The method of claim 32, wherein the figure of merit comprises a thermoelectric figure of merit for a library member.

36. The method of claim 23, wherein identifying a plurality of regions of interest comprises receiving a first user input identifying one or more regions of interest, each region having a user-defined shape, the method further comprising receiving a second user input defining a computation for determining a series of values for each of the one or more regions of interest.

37. The method of claim 36, wherein determining a series of values for each of the one or more regions of interest comprises computing each value in each series in accordance with the second user input.

38. The method of claim 37, wherein the computation is an average for a group of pixels corresponding to a region of interest.

39. The method of claim 23, wherein the plurality of regions of interest is identified after the series of images has been captured.

40. A computer-implemented method for evaluating a combinatorial chemical experiment, comprising:

receiving a series of images of a combinatorial library, the library including a plurality of members, the combinatorial library including a plurality of members, each member being associated with a location in the combinatorial library, the series of images being captured from a first time during the experiment to a second time during the experiment and storing the series of images in memory;

after the series of images has been received, receiving user input identifying a plurality of regions of interest, each region corresponding to a location in each of the series of images and to a location in the combinatorial library; and determining a series of values for one or more regions of interest, the series of values for each of the one or more regions comprising a value for each of the images.

41. The method of claim 40, further comprising calculating from each series of values for the one or more regions a figure of merit for a library member at the corresponding library location.

42. The method of claim 41, further comprising displaying a graphical representation of each figure of merit.

* * * * *

UNITED STATES PATENT AND TRADEMARK OFFICE
CERTIFICATE OF CORRECTION

| | | |
|---|---|---|
| PATENT NO. | : 6,738,529 B1 | Page 1 of 1 |
| APPLICATION NO. | : 09/415772 | |
| DATED | : May 18, 2004 | |
| INVENTOR(S) | : Crevier et al. | |

It is certified that error appears in the above-identified patent and that said Letters Patent is hereby corrected as shown below:

Col. 13, line 32, "corobinatorial" should be replaced with --combinatorial--
Col. 14, line 36, "corobinatorial" should be replaced with --combinatorial--
Col. 15, line 30, "for" should be replaced with --from--

Signed and Sealed this
Fifth Day of April, 2011

David J. Kappos
*Director of the United States Patent and Trademark Office*